US011583376B2

(12) United States Patent
Mori et al.

(10) Patent No.: US 11,583,376 B2
(45) Date of Patent: Feb. 21, 2023

(54) DENTAL GYPSUM SLURRY (71) Applicant: GC Corporation, Tokyo (JP)

(72) Inventors: Daizaburo Mori, Tokyo (JP); Masatoshi Yoshinaga, Tokyo (JP); Kenji Kojima, Tokyo (JP); Kaori Watanabe, Tokyo (JP); Tsukasa Kaneko, Tokyo (JP)

(73) Assignee: GC CORPORATION, Tokyo (JP)

( * ) Notice: Subject to any disclaimer, the term of this patent is extended or adjusted under 35 U.S.C. 154(b) by 437 days.

(21) Appl. No.: 16/621,837

(22) PCT Filed: Jan. 30, 2018

(86) PCT No.: PCT/JP2018/002901
§ 371 (c)(1),
(2) Date: Dec. 12, 2019

(87) PCT Pub. No.: WO2018/230028
PCT Pub. Date: Dec. 20, 2018

(65) Prior Publication Data
US 2021/0085433 A1 Mar. 25, 2021

(30) Foreign Application Priority Data
Jun. 13, 2017 (JP) .............................. JP2017-116349

(51) Int. Cl.
A61K 6/90 (2020.01)
A61C 13/34 (2006.01)
(Continued)

(52) U.S. Cl.
CPC ............ *A61C 13/34* (2013.01); *A61C 13/083* (2013.01); *A61K 6/858* (2020.01); *A61K 6/889* (2020.01);
(Continued)

(58) Field of Classification Search
CPC ....................................................... A61K 6/90
See application file for complete search history.

(56) References Cited

U.S. PATENT DOCUMENTS

2014/0296369 A1* 10/2014 Mori ....................... A61K 6/858
523/116

FOREIGN PATENT DOCUMENTS

CN   102659375 A    9/2012
CN   105198343 A    12/2015
(Continued)

OTHER PUBLICATIONS

International Search Report dated Mar. 27, 2018, issued in counterpart International Application No. PCT/JP2018/002901, with English Translation (2 pages).
"Dentistry—Gypsum products", ISO 6873, (2013), (25 pages).
Miao, Xue et al., "Oral Applied Materials Science", Figure 6-2 on p. 126 cited in CN final rejection dated Jan. 17, 2022, with English Translation. (15 pages).
Final Rejection dated Jan. 17, 2022, issued in counterpart CN application No. 201880038410.1, with English translation. (10 pages).
(Continued)

*Primary Examiner* — Benjamin J Packard
(74) *Attorney, Agent, or Firm* — WHDA, LLP (57) ABSTRACT A dental gypsum slurry includes water and a dental gypsum powder containing hemihydrate gypsum and a polycarboxylic acid salt-based water-reducing agent, wherein a powder-water ratio of the water to the dental gypsum powder is 0.24 to 0.50, and when the water and the dental gypsum powder being mixed are poured up to a height of 50 mm in a cylindrical mold having an inner diameter of 35 mm, which is vertically placed on a flat surface, and then, the cylindrical mold is pulled upward at 10 mm/s at 30 seconds after start of mixing so that a mixture spreads planarly, the diameter of the mixture is 141.4 mm or more.

6 Claims, 4 Drawing Sheets (51) Int. Cl.
    *A61C 13/083*     (2006.01)
    *A61K 6/889*     (2020.01)
    *A61K 6/858*     (2020.01)
    *C04B 11/00*     (2006.01)
    *C04B 24/04*     (2006.01)

(52) U.S. Cl.
    CPC ............... *A61K 6/90* (2020.01); *C04B 11/00* (2013.01); *C04B 24/04* (2013.01)

(56) References Cited

FOREIGN PATENT DOCUMENTS

| | | |
|---|---|---|
| JP | 6-178926 A | 6/1994 |
| JP | 2014-188325 A | 10/2014 |
| JP | 2017-55850 A | 3/2017 |

OTHER PUBLICATIONS

Office Action dated Sep. 23, 2021, issued in counterpart KR Application No. 10-2019-7039014, with machine translation. (9 pages).
Office Action dated Nov. 30, 2021, issued in counterpart JP Application No. 2019-525060, with machine translation. (6 pages).
Office Action dated Jul. 12, 2021, issued in counterpart CN Application No. 201880038410.1, with English Translation. (10 pages).
Extended European Search Report dated Feb. 10, 2021, issued in counterpart EP Application No. 18818368.5. (7 pages).
Office Action dated Jan. 7, 2021, issued in counterpart Chinese Application No. 201880038410.1, with English translation. (18 pages).
Chen Jianzhong, Study on Gypsum—Cement—Fly Ash Self-leveling Materials, Chemical Building Materials, Issue 6, pp. 30-34, with English translation. (17 pages).
Office Action dated Jun. 14, 2022, issued in counterpart BR Application No. BR112019025078-6 , with English Translation. (6 pages).

* cited by examiner

DENTAL GYPSUM SLURRY

TECHNICAL FIELD

The present invention relates to a dental gypsum slurry.

BACKGROUND ART

In recent years, attention is focused on visit medical treatments as a medical form addressing the aging society, and the number of visit medical treatments is increasing. In addition, demand for visit medical treatments is expected to further increase in the future. It is considered that in the dental field, opportunities for dentists to perform visit medical treatments also increase in the future.

One of the operations to be performed in visit medical treatments in the dental field may include producing a dental gypsum model (such as an operational model and a jaw model) which reproduces an intraoral state of a patient. In this operation, a patient's intraoral impression is previously taken with a dental impression material to form a counter mold. In to this counter mold, a dental gypsum slurry obtained by mixing a dental gypsum powder and water is poured. Then, the dental gypsum slurry is set to obtain the above-described gypsum model.

In a known operation for obtaining a dental gypsum slurry in dental clinics and dental laboratories, predetermined amounts of a dental gypsum powder and mixing water are taken into a container such as a compact rubber bowl, and the powder and water are mixed using a gypsum spatula. Since a large number of air bubbles are generated during mixing, contamination of the dental gypsum slurry with air bubbles needs to be suppressed using an apparatus such as a vibrator and a vacuum stirrer.

Patent Literature 1 described below discloses a defoaming method of a dental gypsum slurry. This defoaming method is a method of mixing a dental gypsum slurry using a defoaming device including an antifoaming member and a handle attached to the antifoaming member.

[Patent Literature 1] JPH06-178926 A

SUMMARY OF INVENTION

However, in visit medical treatments, the mixing operation is performed in households which are not provided with apparatuses such as vibrators and vacuum stirrers as well as the defoaming device described in the aforementioned Patent Literature 1. Therefore, there is a demand to produce a dental gypsum model in which air bubbles are suppressed, without using specialized apparatuses such as vibrators and vacuum stirrers.

Thus, an object of the present invention is to provide a gypsum slurry capable of producing a dental gypsum model in which air bubbles are suppressed.

For achieving the above-described object, the dental gypsum slurry according to the present invention includes water and a dental gypsum powder containing hemihydrate gypsum and a polycarboxylic acid salt-based water-reducing agent, in which the powder-water ratio of the water to the dental gypsum powder is 0.24 to 0.50, and when the water and the dental gypsum powder being mixed are poured up to a height of 50 mm in a cylindrical mold having an inner diameter of 35 mm, which is vertically placed on a flat surface, and then, the cylindrical mold is pulled upward at 10 mm/s at 30 seconds after the start of mixing so that the mixture spreads planarly, the diameter of the mixture is 141.4 mm or more.

There has not been known a dental gypsum slurry that has the above-described fluidity at the above-described powder-water ratio. Such a dental gypsum slurry has the above-described fluidity even at 30 seconds after the start of mixing of the dental gypsum powder and the water. Therefore, mixing can be performed by pouring water and a dental gypsum powder into a container such as a sealed bottle and shaking the container, without using a gypsum spatula or the like as in the known dental gypsum slurry. In addition, since the dental gypsum slurry has the above-described fluidity, contamination with air bubbles can be suppressed without using an apparatus such as a vibrator during mixing or while the dental gypsum slurry is poured in a counter mold. According to the dental gypsum slurry of the present invention which has high fluidity and can suppress contamination with air bubbles in this manner, there can be produced a dental gypsum model in which air bubbles are suppressed. It is noted that in the field of a dental gypsum slurry, powder-water ratio is generally defined by a mass of water to a mass of a dental gypsum powder, and is similarly defined in this application.

Furthermore, the powder-water ratio of the water to the dental gypsum powder is preferably 0.24 to 0.34.

With such a powder-water ratio, fluidity can be reduced in an early stage after the start of mixing, and deformation can be suppressed. For example, even if a counter mold is tilted due to external factors or the like after a dental gypsum slurry has been poured in a counter mold, the dental gypsum slurry in the counter mold is inhibited from flowing out of the counter mold.

Furthermore, the setting time of the dental gypsum slurry is preferably 4 minutes and 25 seconds or less from the start of mixing.

There has not been known a dental gypsum slurry that has such short setting time in addition to the above-described fluidity. With such short setting time, a time during which dentists or the like stay in households for producing a dental gypsum model in visit medical treatments as described above can be shortened.

Furthermore, the compressive strength at 1 hour after the start of mixing is preferably 10 MPa or more.

There has not been known a dental gypsum slurry that has such compressive strength while having the above-described fluidity and powder-water ratio. According to such a dental gypsum slurry, the dental gypsum model can have sufficient required mechanical strength.

Furthermore, when the water and the dental gypsum powder being mixed are poured up to a height of 50 mm in a cylindrical mold having an inner diameter of 35 mm, which is vertically placed on a flat surface, and then, the cylindrical mold is pulled upward at 10 mm/s at 90 seconds after the start of mixing, a spread in a diameter direction is preferably 2% or less.

When fluidity is low in a short time after the start of mixing in this manner, deformation can be suppressed.

The linear expansion coefficient at 2 hours after the start of mixing relative to at the start of mixing is preferably 0.10% to 0.15%. The linear expansion coefficient at 24 hours after the start of mixing relative to at the start of mixing is preferably 0.10% to 0.20%.

When the linear expansion coefficient is low in this manner, a dental prosthetic appliance can be produced using a dental gypsum model to produce a dental prosthetic appliance having a small error.

As described above, according to the present invention, there is provided a dental gypsum slurry capable of producing a dental gypsum model in which air bubbles are suppressed.

DESCRIPTION OF EMBODIMENTS

Embodiments of the dental gypsum slurry according to the present invention will be exemplified below. The embodiments exemplified below are for facilitating the understanding of the present invention, and not for interpreting the present invention in a limited manner. The following embodiments can be modified or improved without departing from the scope of the present invention.

The dental gypsum slurry according to the present embodiment includes water and a dental gypsum powder containing hemihydrate gypsum and a polycarboxylic acid salt-based water-reducing agent.

Examples of the hemihydrate gypsum may include a hemihydrate gypsum, β hemihydrate gypsum, and a mixture of a hemihydrate gypsum and β hemihydrate gypsum.

Examples of the polycarboxylic acid salt-based water-reducing agent may include: polycarboxylate ether; water-soluble salt of a copolymer of chain olefin having 5 or 6 carbon atoms and ethylene-based unsaturated carboxylic acid anhydride; a copolymer of polyethylene glycol mono-allyl ether and unsaturated dicarboxylic acid; a copolymer of polyalkylene glycol mono(meth)acrylic acid ester and (meth)acrylic acid; a copolymer of (meth)acrylic acid amide having a sulfone group at the terminal, acrylic acid ester, and (meth)acrylic acid; a copolymer of a monomer having a sulfone group such as vinyl sulfonate, aryl sulfonate, and methacryl sulfonate, (meth)acrylic acid, and another monomer; a copolymer of a monomer having an aromatic ring substituted with a sulfone group and maleic acid; and a four-party copolymer of a monomer having a sulfone group at the terminal, polyalkylene glycol mono(meth)acrylic acid ester, polyalkylene glycol mono(meth)acrylic acid ether, and (meth)acrylic acid.

The content of the polycarboxylic acid salt-based water-reducing agent relative to 100 parts by mass of the hemihydrate gypsum is preferably 0.05 to 0.8 parts by mass, more preferably 0.15 to 0.3 parts by mass, further preferably 0.15 to 0.25 parts by mass. When the content of the polycarboxylic acid salt-based water-reducing agent relative to 100 parts by mass of the hemihydrate gypsum is 0.05 parts by mass or more, fluidity is further excellent, and contamination with air bubbles can be further suppressed. Furthermore, when the content of the polycarboxylic acid salt-based water-reducing agent is 0.8 parts by mass or less, the durability of the set body after the gypsum slurry has been set can be maintained favorable.

The dental gypsum powder according to the present embodiment preferably contains dihydrate gypsum in addition to the above-described hemihydrate gypsum and polycarboxylic acid salt-based water-reducing agent. The inclusion of the dihydrate gypsum can promote the setting of the gypsum slurry. When the dihydrate gypsum is contained, the content of the dihydrate gypsum relative to 100 parts by mass of the hemihydrate gypsum is preferably 2 to 4 parts by mass, more preferably 2 to 3.5 parts by mass, further preferably 2 to 3 parts by mass. When the dihydrate gypsum is contained in this manner, and the content of the dihydrate gypsum relative to 100 parts by mass of the hemihydrate gypsum is 2 parts by mass or more, the setting of the gypsum slurry can be further promoted. Furthermore, when the content is 4 parts by mass or less, the reduction in fluidity of the gypsum slurry and the expansion due to setting can be suppressed. Thus, the accuracy of the obtained dental gypsum model can be improved.

Examples of the dihydrate gypsum may include natural gypsum and chemical gypsum. Examples of the chemical gypsum may include gypsum newly synthesized from sulfuric acid and calcium carbonate, and byproduct gypsum obtained as byproducts of various chemical processes. Although the average particle sizes of the above-described chemical gypsums are roughly 30 μm to 60 μm, the dental gypsum powder according to the present embodiment may include dihydrate gypsum containing crystals having an average particle size of more than 60 μm.

Furthermore, the dental gypsum powder according to the present embodiment preferably contains potassium sulfate. The inclusion of the potassium sulfate in the dental gypsum powder can suppress setting expansion. When the dental gypsum powder contains the potassium sulfate, the content of the potassium sulfate relative to 100 parts by mass of the hemihydrate gypsum is preferably 0.5 to 3 parts by mass. When the content of the potassium sulfate relative to 100 parts by mass of the hemihydrate gypsum is 0.5 parts by mass or more, setting expansion can be more suppressed. When the content of the potassium sulfate is 3 parts by mass or less, excessive promotion of setting can be suppressed. The content of the potassium sulfate relative to 100 parts by mass of the hemihydrate gypsum is more preferably 0.5 to 2 parts by mass.

It is noted that when the dental gypsum powder contains the dihydrate gypsum as described above, the content of the potassium sulfate may be determined based on the content of the dihydrate gypsum. In this case, the content of the potassium sulfate relative to 100 parts by mass of the dihydrate gypsum is preferably 25 to 100 parts by mass, from the viewpoint of achieving setting expansion that is appropriate as a dental gypsum model.

The dental gypsum powder according to the present embodiment may further contain: a setting expansion inhibitor such as sodium sulfate and potassium tartrate; a coloring agent; a weight reducer; and a known setting retarder such as salts (for example, citric acid salt, boric acid salt, and acetic acid salt) and water-soluble polymers (for example, starch, gum arabic, carboxymethylcellulose, and gelatin).

The amount of water included in the dental gypsum slurry according to the present embodiment is 0.24 to 0.50 parts by mass relative to 100 parts by mass of the dental gypsum powder. That is, the powder-water ratio of the water to the dental gypsum powder is 0.24 to 0.50. Furthermore, the powder-water ratio being 0.24 to 0.34 is preferable, from the viewpoint of reducing fluidity in an early stage after the start of mixing, and suppressing deformation. When fluidity decreases in an early stage after the start of mixing, the dental gypsum slurry in a counter mold is inhibited from flowing out of the counter mold, even if, for example, the counter mold is tilted due to external factors or the like after the dental gypsum slurry has been poured in the counter mold.

In this way, the dental gypsum slurry according to the present embodiment exhibits high fluidity at a predetermined powder-water ratio. Specifically, as illustrated in the following examples, the dental gypsum slurry according to the present embodiment has a powder-water ratio of the water to the dental gypsum powder of 0.24 to 0.50 as described above. Furthermore, the dental gypsum slurry has fluidity in which when the dental gypsum powder and the water are poured up to a height of 50 mm in a cylindrical mold having an inner diameter of 35 mm, which is vertically placed on a flat surface, and then, the cylindrical mold is pulled upward at 10 mm/s at 30 seconds after the start of mixing so that the mixture spreads planarly, the diameter of the mixture is 141.4 mm or more.

Furthermore, since the dental gypsum slurry according to the present embodiment has high fluidity as described above, the dental gypsum powder and the water can be mixed by pouring them in a container such as a bottle, and sealing and shaking the container.

An example of the container used in mixing the dental gypsum slurry according to the present embodiment is a bottle-like container that has a cap and a closed-end cylindrical container body having an opening. The cap can block the opening of the container body to seal the container.

As described herein, sealing refers to airtightness in which when a dental gypsum powder and water are placed in a container, the opening is blocked by a cap, and the container is shaken, the dental gypsum powder and water do not leak to the outside. The shape of the cap, the fixing method between the cap and the container body, and the like are not particularly limited, as long as the cap is capable of such sealing.

The inner diameter of the opening of the container is not particularly limited, as long as it allows the dental gypsum powder and water to enter and the dental gypsum slurry to leave. For example, the inner diameter is 1 cm to 20 cm.

The volume of the container is preferably, but not particularly limited to, 0.01 L to 1 L, in consideration of, for example, the required amount of the dental gypsum slurry per use in visit medical treatments.

Furthermore, the container is preferably transparent or translucent at least partly so that the inside of the container can be visually recognized.

Examples

Although the present invention will be more specifically described below with reference to examples, the present invention is not limited to the following examples.
<Preparation of Dental Gypsum Powder>

With respect to 100 parts by mass of hemihydrate gypsum, there were prepared 0.15 parts by mass of a polycarboxylic acid salt-based water-reducing agent, 2 parts by mass of dihydrate gypsum, 0.8 parts by mass of potassium sulfate, and 0.01 parts by mass of sodium sulfate. These raw materials were poured in a pot mill, and blended for 60 minutes to prepare a dental gypsum powder.

As the polycarboxylic acid salt-based water-reducing agent, Melflux 2651F was used. The "Melflux 2651F" is a polycarboxylic acid salt-based water-reducing agent manufactured by BASF Co. which primarily contains polycarboxylate ether.

<Mixing of Dental Gypsum Powder>

A dental gypsum slurry of Sample 1 was obtained by pouring 124 g in total of the produced dental gypsum powder and water in a polystyrene resin cylindrical vial (inner diameter of opening: about 4 cm, height: about 7 cm, volume: about 90 mL, mass: about 25 g, wall thickness: about 1.5 mm) such that the powder-water ratio to the dental gypsum powder became 0.24, sealing the vial, and shaking the vial by the hand for 20 seconds. Similarly, a dental gypsum slurry of Sample 2 was obtained such that the powder-water ratio to the produced dental gypsum powder became 0.25; a dental gypsum slurry of Sample 3 was obtained such that the powder-water ratio to the produced dental gypsum powder became 0.34; and a dental gypsum slurry of Sample 4 was obtained such that the powder-water ratio to the produced dental gypsum powder became 0.50.
<Evaluation of Fluidity>

A ring mold having an inner diameter of 35 mm and a height of 50 mm was vertically set up on a flat surface. In the ring mold, the dental gypsum slurry of Sample 1 obtained by mixing was poured up to a height of 50 mm. Next, the ring mold was pulled upward at 10 mm/s at 30 seconds after the start of mixing. Due to this action, the dental gypsum slurry spread planarly from the bottom of the ring mold. The diameter of this spread dental gypsum slurry was measured. In addition, a similar measurement was performed for the dental gypsum slurries of Samples 2 to 4. Furthermore, for the dental gypsum slurries of Samples 2 to 4, a similar measurement was performed by pulling the ring mold upward at 10 mm/s at 45 seconds, 60 seconds, 75 seconds, and 90 seconds after the start of mixing. The measurement results are illustrated in FIG. 1.

For the dental gypsum slurry of Sample 1 having a powder-water ratio of 0.24, the diameter of a planar spread caused by pulling the ring mold upward at 10 mm/s at 30 seconds after the start of mixing as described above was 141.4 mm. Furthermore, as illustrated in FIG. 1, for the dental gypsum slurries of Samples 2 to 4 having a powder-water ratios being higher than Sample 1, the diameters when the ring mold was pulled upward at 10 mm/s at 30 seconds after the start of mixing were also 141.4 mm or more.

Figure 1:
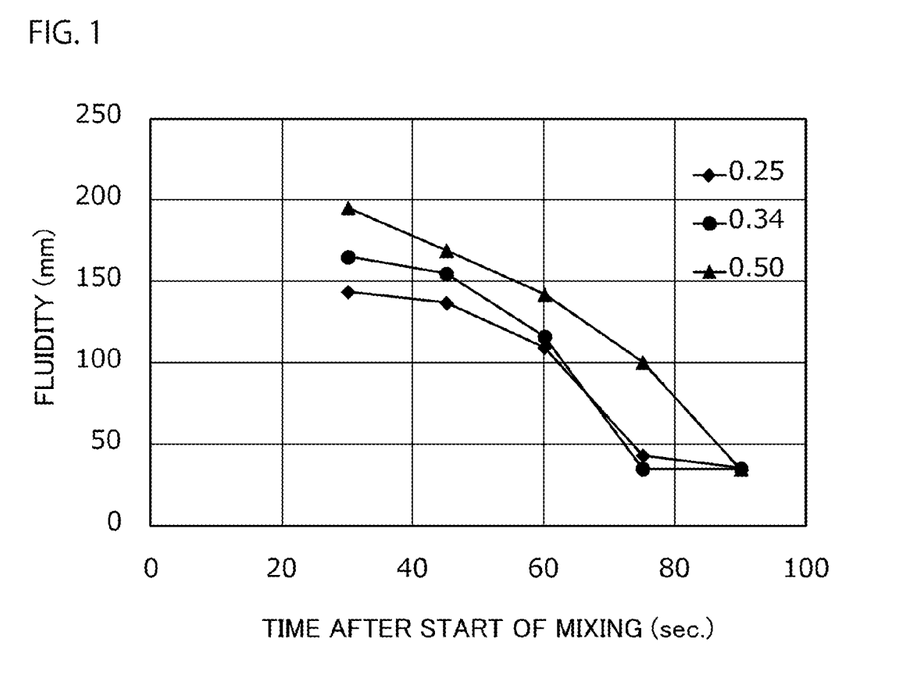
FIG. 1 is a diagram illustrating evaluation results for fluidity of dental gypsum slurries according to Examples.

Furthermore, as illustrated in FIG. 1, the diameter when the ring mold was pulled upward at 10 mm/s at 75 seconds after the start of mixing was 43.3 mm for the dental gypsum slurry of Sample 2 having a powder-water ratio of 0.25, and 35.2 mm for the dental gypsum slurry of Sample 3 having a powder-water ratio of 0.34. This demonstrated that for the dental gypsum slurries of Samples 2 and 3, fluidity extremely decreases at 75 seconds after the start of mixing. From this tendency, it can be estimated that the same applies for the dental gypsum slurry of Sample 1 having a powder-water ratio of 0.24. That is, when the dental gypsum slurry of the present example has a powder-water ratio of 0.24 to 0.34, fluidity can be reduced in an early stage after the start of mixing, and deformation can be suppressed. For example, even if a counter mold is tilted due to external factors or the like after a dental gypsum slurry having such a powder-water ratio has been poured in the counter mold, the dental gypsum slurry in the counter mold can be inhibited from flowing out of the counter mold.

Furthermore, as illustrated in FIG. 1, the diameter when the ring mold was pulled upward at 10 mm/s at 90 seconds after the start of mixing was 35.7 mm for the dental gypsum slurry of Sample 2 having a powder-water ratio of 0.25; 35.2 mm for the dental gypsum slurry of Sample 3 having a powder-water ratio of 0.34; and 35.2 mm for the dental gypsum slurry of Sample 4 having a powder-water ratio of 0.50. That is, the results were that for each of the dental gypsum slurries of Samples 2 to 4, a change in diameter when the ring mold was pulled upward at 10 mm/s at 90 seconds after the start of mixing was 2% or less. From this tendency, it can be estimated that the same result can be obtained for the dental gypsum slurry of Sample 1. That is, when the dental gypsum slurry of the present example has a powder-water ratios of 0.24 to 0.34, low fluidity can be quickly achieved, and deformation due to external factors or the like can be suppressed.

<Evaluation of Presence or Absence of Air Bubbles>

Each of the dental gypsum slurries of Samples 1 to 4 was poured in an impression material. After 10 minutes, a gypsum model was removed from the impression material. The presence or absence of air bubbles was visually evaluated for the obtained gypsum model. As a result, air bubbles were not confirmed in any of Samples. It is considered that this is attributable to the fact that Samples 1 to 4 each have high fluidity as described above.

<Measurement of Setting Time>

Next, setting time was measured for the dental gypsum slurries of Samples 2 to 4, by a method defined in ISO 6873:2013 "Dentistry-Gypsum products". Specifically, using a Vicat needle apparatus, the dental gypsum slurry of each of Samples 2 to 4 was poured in a ring mold, and the upper surface was flattened. Then, a Vicat needle was allowed to gently descend to the dental gypsum slurry, and the time until the penetration depth of the Vicat needle became 2 mm or less was measured. This measured time was defined as setting time. The diameter of the tip of the Vicat needle was 1 mm, and 300 g force was applied downward to the tip of the Vicat needle. In addition, the ring mold had an inner diameter of 20 mm and a height of 30 mm. The results are illustrated in FIG. 2.

Figure 2:
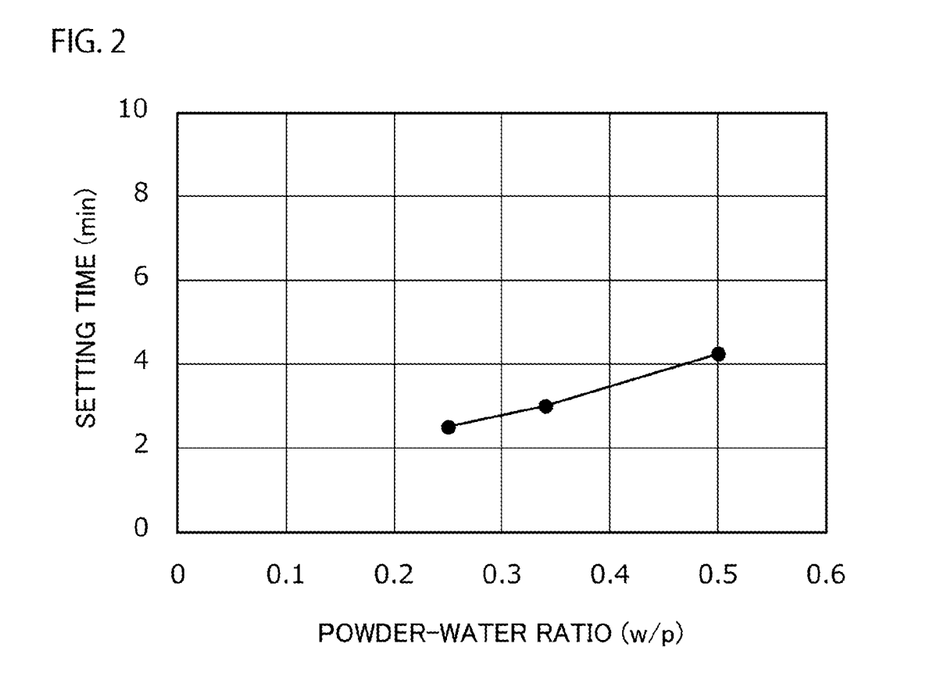
FIG. 2 is a diagram illustrating measurement results for setting time of dental gypsum slurries according to Examples.

As illustrated in FIG. 2, the setting time was 4 minutes and 25 seconds for the dental gypsum slurry of Sample 4 having the highest powder-water ratio, and was less than 4 minutes and 25 seconds for other Samples. Therefore, it is considered that the setting time is also less than 4 minutes and 25 seconds for the dental gypsum slurry of Sample 1. There has not been known a dental gypsum slurry that has high fluidity as described above and short setting time in this manner. When the setting time is short in this manner, a time during which a dentist or the like stays in a household for producing a dental gypsum model in a visit medical treatment can be shortened.

<Evaluation of Strength of Gypsum Set Body>

Figure 3:
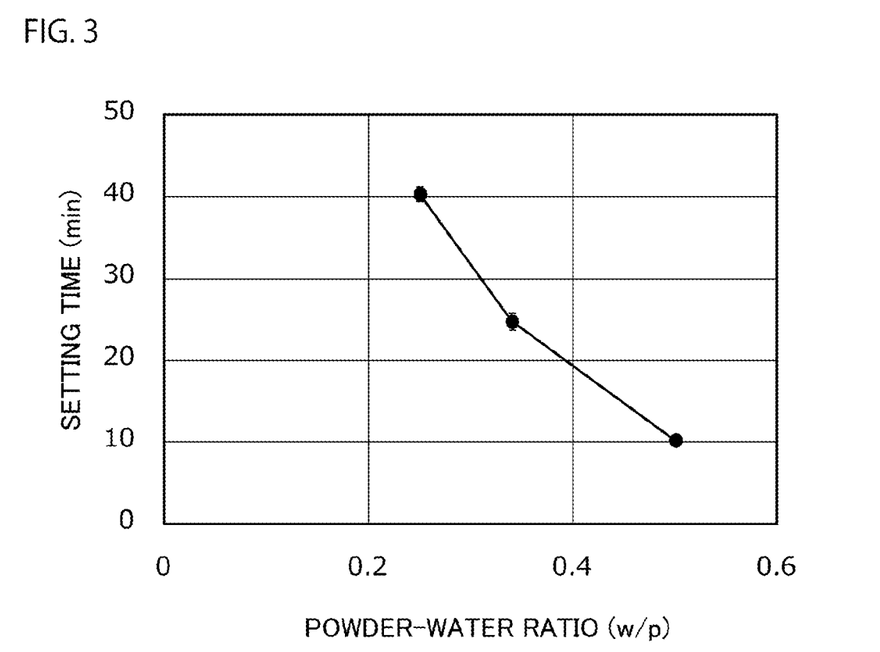
FIG. 3 is a diagram illustrating evaluation results for strength of gypsum set bodies obtained by setting dental gypsum slurries according to Examples.

Next, compressive strength was measured for a gypsum set body produced with each of the dental gypsum slurries of Samples 2 to 4, by applying load at 60 minutes after the start of mixing in accordance with a method defined in ISO 6873:2013 "Dentistry-Gypsum products". Specifically, each of the dental gypsum slurries of Samples 2 to 4 was poured up to a height of 40 mm into a cylindrical space having an inner diameter of 20 mm formed inside a split mold, and set to produce a cylindrical gypsum set body having a diameter of 20 mm and a height of 40 mm. The upper and lower surfaces of this gypsum set body were pressed by a metal die having a flat surfaces, so that force was added to this gypsum set body in a height direction at a rate of 5 kN/min at 60 minutes after the start of mixing of the dental gypsum slurry. The maximum compressive strength to cause the gypsum set body to rupture was calculated according to the following formula.

$$\text{Compressive strength(MPa)} = \text{Maximum force(N)} / \text{Area of gypsum set body}$$

The results of this evaluation are illustrated in FIG. 3.

As illustrated in FIG. 3, the gypsum set bodies produced with the dental gypsum slurries of Samples 2 to 4 had a compressive strength of more than 10 MPa. There has not been known a dental gypsum slurry that has such compressive strength while having the above-described fluidity and powder-water ratio. According to such a dental gypsum slurry, the dental gypsum model can have sufficient required mechanical strength. Notably, the gypsum set body produced with the dental gypsum slurry of Sample 2 having a powder-water ratio of 0.25 had a compressive strength of more than 40 MPa, demonstrating that it satisfied the standard of Type 4 (super-hard gypsum) defined in ISO 6873:2013 "Dentistry-Gypsum products". Accordingly, it is estimated that the gypsum set body produced with the dental gypsum slurry of Sample 1 also has a compressive strength of more than 40 MPa.

<Evaluation of Liner Setting Expansion>

Next, linear setting expansion was measured for the dental gypsum slurries of Samples 2 to 4, by a method defined in ISO 6873:2013 "Dentistry-Gypsum products". Specifically, each of the dental gypsum slurries of Samples 2 to 4 was poured in a square cross-section layer having a width of 20 mm, a depth of 20 mm, and a length of 100 mm, and the initial value length of the dental gypsum slurry was measured at the start of mixing. Next, the length of a gypsum set body as a set body of the dental gypsum slurry was measured at 2 hours and 24 hours after the start of mixing, and linear expansion coefficients to the initial value length were calculated. The results are illustrated in FIG. 4.

Figure 4:
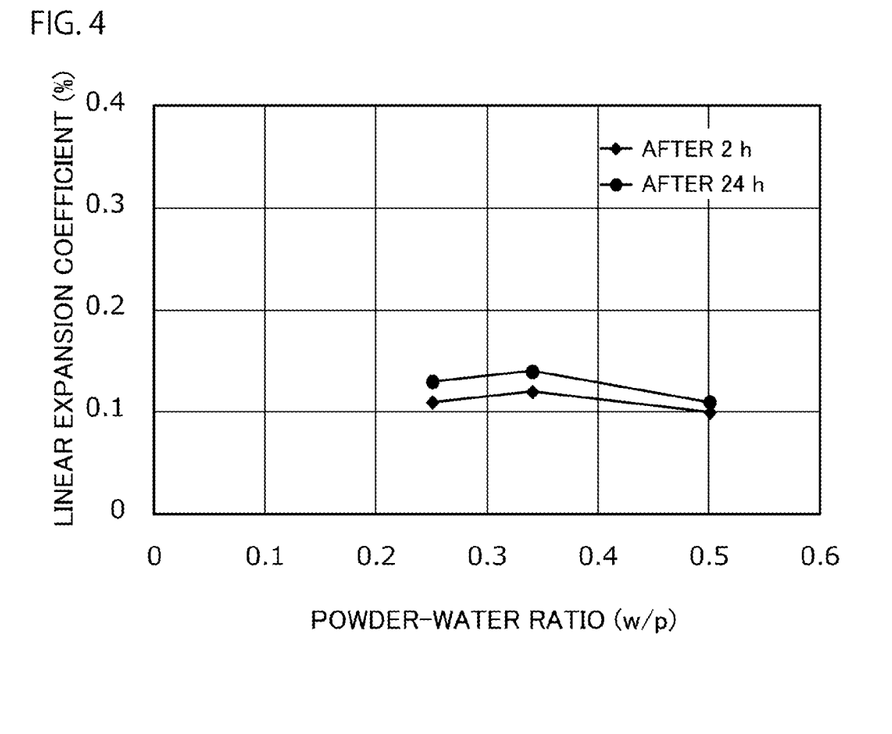
FIG. 4 is a diagram illustrating evaluation results for linear setting expansion of gypsum set bodies obtained by setting dental gypsum slurries according to Examples.

As illustrated in FIG. 4, the linear expansion coefficients at 2 hours after the start of mixing relative to at the start of mixing were 0.10% to 0.12% for the dental gypsum slurries of Samples 2 to 4. Furthermore, the linear expansion coefficients at 24 hours after the start of mixing relative to at the start of mixing were 0.13% to 0.14% for the dental gypsum slurries of Samples 2 to 4. These results demonstrated that the dental gypsum slurries of Samples 2 to 4 had extremely small linear expansion coefficients. From this tendency, it is estimated that the dental gypsum slurry of Sample 1 also has an extremely small linear expansion coefficient. With such low linear expansion coefficients, a dental prosthetic appliance can be produced using a dental gypsum model, so that a dental prosthetic appliance having a small error is produced. From such a viewpoint, the linear expansion coefficient at 2 hours after the start of mixing relative to at the start of mixing is preferably 0.10% to 0.15%, and the linear expansion coefficient at 24 hours after the start of mixing relative to at the start of mixing is preferably 0.10% to 0.20%, although different from FIG. 4.

From the above-described examples, it was confirmed that a dental gypsum model in which air bubbles are suppressed can be produced, when a dental gypsum slurry includes water and a dental gypsum powder containing hemihydrate gypsum and a polycarboxylic acid salt-based water-reducing agent, in which the powder-water ratio of the water to the dental gypsum powder is 0.24 to 0.50, and when the water and the dental gypsum powder being mixed are poured up to a height of 50 mm in a cylindrical mold having an inner diameter of 35 mm, which is vertically placed on a flat surface, and then, the cylindrical mold is pulled upward at 10 mm/s at 30 seconds after the start of mixing so that the mixture spreads planarly, the diameter of the mixture is 141.4 mm or more.

According to the present invention, there is provided a dental gypsum slurry capable of producing a dental gypsum model in which air bubbles are suppressed. The dental gypsum slurry can be used in the field of the production of a dental gypsum model.

The invention claimed is:

1. A dental gypsum slurry comprising water and a dental gypsum powder containing hemihydrate gypsum and a polycarboxylic acid salt-based water-reducing agent, wherein
   a powder-water ratio of the water to the dental gypsum powder is 0.34 to 0.50, and
   when the water and the dental gypsum powder being mixed are poured up to a height of 50 mm in a cylindrical mold having an inner diameter of 35 mm, which is vertically placed on a flat surface, and then, the cylindrical mold is pulled upward at 10 mm/s at 30 seconds after start of mixing so that a mixture spreads planarly, the diameter of the mixture is 141.4 mm or more.

2. The dental gypsum slurry according to claim 1, wherein setting time is 4 minutes and 25 seconds or less from start of mixing.

3. The dental gypsum slurry according to claim 1, wherein compressive strength at 1 hour after start of mixing is 10 MPa or more.

4. The dental gypsum slurry according to claim 1, wherein when the water and the dental gypsum powder being mixed are poured up to a height of 50 mm in a cylindrical mold having an inner diameter of 35 mm, which is vertically placed on a flat surface, and then, the cylindrical mold is pulled upward at 10 mm/s at 90 seconds after start of mixing, a spread in a diameter direction is 2% or less.

5. The dental gypsum slurry according to claim 1, wherein linear expansion coefficient at 2 hours after start of mixing relative to at start of mixing is 0.10% to 0.15%.

6. The dental gypsum slurry according to claim 5, wherein linear expansion coefficient at 24 hours after start of mixing relative to at start of mixing is 0.10% to 0.20%.

* * * * *